United States Patent [19]

Habeeb

[11] Patent Number: 4,501,677

[45] Date of Patent: Feb. 26, 1985

[54] HETEROCYCLIC NITROGEN COMPOUNDS—ORGANOMETALLIC SALT COMPLEXES AS CORROSION INHIBITORS IN LUBRICATING OILS

[75] Inventor: Jacob J. Habeeb, Sarnia, Canada

[73] Assignee: Exxon Research & Engineering Co., Florham Park, N.J.

[21] Appl. No.: 547,984

[22] Filed: Nov. 2, 1983

[51] Int. Cl.$^3$ .................. C10M 1/32; C10M 1/54
[52] U.S. Cl. .................. 252/37.2; 252/40.7; 252/42.1; 252/42.7; 252/51.5 R; 252/51.5 A; 252/392
[58] Field of Search ........... 252/42.7, 51.5 A, 51.5 R, 252/37.2, 40.7, 42.1, 392

[56] References Cited

U.S. PATENT DOCUMENTS

| | | | |
|---|---|---|---|
| 1,768,910 | 7/1930 | Ihrig | 252/390 |
| 2,060,138 | 11/1936 | Taylor | 252/390 |
| 2,270,241 | 1/1942 | Adams et al. | 252/37 |
| 2,296,342 | 9/1942 | Gaylor et al. | 252/390 |
| 2,468,163 | 4/1949 | Blair, Jr. et al. | 252/390 |
| 2,618,608 | 11/1952 | Schaeffer | 252/390 |
| 2,987,522 | 6/1961 | Shen | 252/390 |
| 3,018,248 | 1/1962 | Foehr | 252/37 |
| 3,197,408 | 7/1965 | Cupper et al. | 252/51.5 A |
| 3,294,705 | 12/1966 | Kautsky | 252/390 |
| 3,481,978 | 12/1969 | Sparks | 252/390 |
| 3,642,847 | 2/1972 | Otto et al. | 252/42.7 |
| 4,338,207 | 7/1982 | Adams | 252/42.7 |
| 4,431,553 | 2/1984 | Fodor et al. | 252/42.7 |
| 4,464,276 | 8/1984 | Sung et al. | 252/42.7 |

Primary Examiner—Jacqueline V. Howard
Attorney, Agent, or Firm—Eugene Zagarella

[57] ABSTRACT

A lubricating oil composition with improved corrosion inhibiting properties comprising a major amount of a lubricating oil basestock and an effective amount of a complex of a selected heterocyclic nitrogen compound and an organometallic salt of a $C_4$ to $C_{22}$ fatty acid.

11 Claims, No Drawings

HETEROCYCLIC NITROGEN COMPOUNDS—ORGANOMETALLIC SALT COMPLEXES AS CORROSION INHIBITORS IN LUBRICATING OILS

BACKGROUND OF THE INVENTION

This invention relates to a lubricating oil composition containing a complex of a selected heterocyclic nitrogen compound and an oil soluble organometallic salt as a corrosion inhibitor.

The use of additives such as corrosion inhibitors in lubricating oil compositions has been widespread for a good many years. Some of the representative types of corrosion inhibitors used in lubricating oils are noted in "Lubricant Additives" by C. V. Smalheer and R. K. Smith, 1967, p. 6 and include metal dithiophosphates, metal dithiocarbamates, sulfurized terpenes and phosphosulfurized terpenes.

A variety of nitrogen containing compounds have been disclosed to be useful as corrosion inhibitors or as additives for other purposes in hydrocarbon compositions. U.S. Pat. No. 1,768,910 discloses the use of nitrogeneous base compounds such as pyridine, quinoline and piperidine as corrosion inhibitors in oil compositions. U.S. Pat. No. 2,060,138 discloses the combination of cyclohexylamine with various soaps to produce corrosion inhibitors for alcohol solutions. U.S. Pat. No. 2,296,342 discloses an oil composition with improved corrosion properties containing an oil soluble amine compound such as benzidine, toluidine and xylidine and an oil soluble ester of an acid. U.S. Pat. No. 2,468,163 discloses the use of cyclic amidines and in particular substituted imidazolines as corrosion inhibitors. U.S. Pat. No. 2,618,608 discloses the use of selected cyclic nitrogen compounds such as adenine as discoloration inhibitors in detergent compositions. U.S. Pat. No. 2,987,522 discloses the use of selected azaalkylene substituted cyclic amidines as corrosion inhibitors. U.S. Pat. No. 3,197,408 discloses synthetic ester lubricating oils with improved anti-corrosion properties containing selected nitrogen-containing heterocyclic compounds such as benzimidazole and cyanuric acid. U.S. Pat. No. 3,294,705 discloses the use of mixtures of selected aminoamides and salts of said aminoamides to inhibit corrosion in petroleum refining operations.

Other additives disclosed to be useful in lubricating oil compositions include: phosphatides as solubilizers for metal salts of carboxylic acids in U.S. Pat. No. 2,270,241; select copper and cobalt salts of organic acids in oils containing phenols to enhance the oxidation inhibition properties as shown in U.S. Pat. No. 3,018,248; and substituted benzodiazoboroles as oxidation inhibitors as disclosed in U.S. Pat. No. 3,481,978.

Despite the variety of known additives that are available, there is still the need and desire to find additional compounds having improved properties particularly as corrosion inhibitors in lubricating oil systems.

SUMMARY OF THE INVENTION

Now in accordance with this invention it has been found that complexes of selected heterocyclic nitrogen compounds and oil soluble organometallic salts are especially useful as corrosion inhibitors in lubricating oil compositions. More particularly this invention relates to a lubricating oil composition comprising a major amount of a lubricating oil basestock and an effective amount of a corrosion inhibitor comprising a complex of:

(a) a heterocyclic nitrogen compound having the formula:

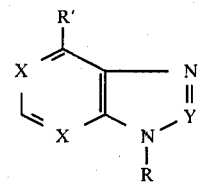

wherein each x is C or N with at least one x being N; Y is C or N; R is H, alkyl of 1 to 20 carbons or $CH_2NR''_2$ where each R'' is H or alkyl of 1 to 20 carbons; and R' is H, alkyl of 1 to 20 carbons or $NR'''_2$ with each R''' being H or alkyl of 1 to 20 carbons; and (b) an oil soluble organometallic salt of a $C_4$–$C_{22}$ fatty acid where the metal is selected from the group consisting of nickel, copper, zinc, molybdenum, calcium and sodium.

DETAILED DESCRIPTION OF THE INVENTION

This invention, as noted above, is directed to lubricating oil compositions which contain selected complexes of a heterocyclic nitrogen compound and an organometallic salt to provide improved corrosion inhibiting properties.

The particular heterocyclic nitrogen compound used in forming the complex of this invention has the following general formula:

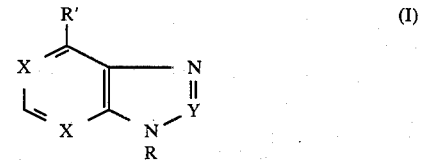

wherein each x is C or N with at least one x being N; Y is C or N; R is H, alkyl of 1 to 20 carbons or $CH_2NR''_2$ where each R'' is H or alkyl of 1 to 20 carbons; and R' is H, alkyl of 1 to 20 carbons or $NR'''_2$ with each R''' being H or alkyl of 1 to 20 carbons. Preferably, both x groups will be N, Y will be C and the alkyl groups in R'' and R''' will contain 8 to 16 carbon atoms. Additional substituent groups, for example, alkyl groups, may be added at other places on the ring structure (I) and other types of substituents besides those noted above may also be used to provide such compounds (I) with added oil solubility.

Illustrative compounds of the type identified by general formula (I) include purine, 6-aminopurine, 4-azabenzimidazole, 8-azaadenine, 9-diethylaminomethylpurine, 9-dibutylaminomethylpurine, 9-dioctylaminomethylpurine and 9-didodecylaminomethylpurine. Preferred compounds (I) are purine and 6-aminopurine with 6-aminopurine being particularly preferred.

The oil soluble organometallic salts which are useful in this invention include any salts that complex with the selected heterocyclic nitrogen compound and generally will have the formula:

$$M(O\overset{O}{\overset{\|}{C}}R)_x \quad \text{(II)}$$

where M may be any metal that forms an oil soluble acid salt and more particularly is an alkali metal, alkaline earth metal or transition metal selected from the group consisting of sodium, potassium, calcium, magnesium, chromium, manganese, iron, nickel, molybdenum, copper, zinc, tin and lead; R is the hydrocarbon portion of an organo acid, generally a fatty acid of 4 to 22 carbons; and x is an integer equal to the valence of the metal M.

Preferred metals M used in the organometallic salt (II) are nickel, copper, zinc, molybdenum, calcium and sodium with copper and zinc being most preferred. Generally the R group used in the organometallic salt (II) will be the hydrocarbon portion of linear or branched $C_4$ to $C_{22}$ fatty acids, its isomers and mixtures thereof and also may be "Tall oil" or "Naphthenic acid".

"Tall oil" is a well known commodity and is a commercially available mixture of rosin acids, fatty acids and other materials obtained by the acid treatment of the alkaline liquors from the digesting of pine wood.

"Naphthenic acid" is a general term for saturated higher fatty acids derived from the gas-oil fraction of petroleum by extraction with caustic soda solution and subsequent acidification.

The preferred R groups used in salt (II) are $C_6$–$C_{20}$ linear or branched fatty acids and most preferred are the $C_{14}$–$C_{20}$ fatty acids. Illustrative acids are butyric, isobutyric, pentanoic, hexanoic, octanoic, 2-ethylhexanoic, decanoic, dodecanoic, myristic, palymitic, stearic, behenic, linoleic and oleic. Oleic acid is a particularly preferred acid.

In forming the complex by combining the heterocyclic nitrogen compound (I) with organometallic salt (II), the amount of each compound used will vary depending on the nature of each compound and particularly the number of nitrogen atoms available for coordinating with the metal salt. Generally up to about 3 moles of nitrogen containing compound per mole of salt will be used and preferably about 1 to 2 moles of nitrogen containing compound per mole of salt will be used. The amounts as described above are stoichiometric amounts and generally in forming the complex, an excess of such stoichiometric amounts can be used.

The lubricating oil basestock which comprises the major portion, i.e. at least 50% by weight of the oil composition are the typical and conventionally used lubricating oils and include the mineral and synthetic lubricating oils and mixtures thereof. The synthetic oils include diester oils such as di(2-ethylexyl)sebacate, azelate and adipate; complex ester oils such as those formed from dicarboxylic acids, glycols and either monobasic acids or monohydric alcohols; silicone oils; sulfide esters; organic carbonates and other synthetic oils known to the art.

The amount of complex used in the lubricating oil composition in accordance with this invention will generally be an effective corrosion inhibiting amount. Generally from about 0.05 to 2% and preferably from about 0.1 to about 1% by weight of complex will be used, said weight based on the total weight of the lubricating oil composition.

Other additives may of course be added to the compositions of this invention and this includes the conventionally known additives used in lubricating oils.

The following example is further illustrative of this invention and is not intended to be construed as a limitation thereof.

EXAMPLE

A complex of copper oleate and adenine was prepared by stirring 0.34 g. adenine in 6.8 g. of copper oleate at 135°–140° C. for 30 minutes with a greenish-blue oil soluble liquid being formed.

The corrosion inhibition properties of the copper oleate-adenine complex was demonstrated in a beaker oven test, a laboratory test developed to simulate field results. It involved immersing a copper foil specimen (6 cm × 5 cm, 0.00254 cm thick) in 200 cc of a conventional formulated engine lubricating oil at 115° C. for 120 hours. Results are shown in the table that follows.

These results indicate that the use of the copper oleate-adenine complex significantly reduces the amount of copper corrosion formed not only when compared to the sample using just the reference lubricating oil, but also when the oil contained either the copper oleate or the adenine compounds alone.

TABLE

|  |  | Reference Oil | Reference Oil + 0.5 wt. % Copper Oleate | Reference Oil + 0.5 wt. % Copper Oleate-Adenine Complex Containing 0.025 wt. % Adenine | Reference Oil + 0.025 wt. % Adenine |
|---|---|---|---|---|---|
| Copper, ppm in used oil | Before Test | Zero | 132 | 143 | Zero |
|  | After Test | 115 | 196 | 146 | 109 |
| Copper Specimen |  | Heavy Tarnish | Medium Tarnish | No Tarnish (Bright Surface) | Heavy Tarnish |

What is claimed is:

1. A lubricating oil composition comprising a major amount of a lubricating oil basestock and an effective amount of a corrosion inhibitor comprising a complex of:

(a) a heterocyclic nitrogen compound having the formula:

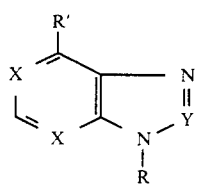

where each x is C or N with at least one x being N; Y is C or N; R is H, alkyl of 1 to 20 carbons or $CH_2NR''_2$ where each R'' is H or alkyl of 1 to 20 carbons; and R' is H, alkyl of 1 to 20 carbons or NR'''$_2$ with each R''' being H or alkyl of 1 to 20 carbons; and (b) an oil soluble organometallic salt having the formula:

$$M(OCR)_x$$

where M is an alkali metal, alkaline earth metal or transition metal selected from the group consisting of sodium, potassium, calcium, magnesium, chromium, manganese, iron, nickel, molybdenum, copper, zinc, tin and lead; R is the hydrocarbon portion of a linear or branched $C_4$ to $C_{22}$ fatty acid and x is an integer equal to the valence of the metal M.

2. The composition of claim 1 wherein from about 0.05 to about 2% by weight of said complex, based on the total weight of the lubricating oil composition is used.

3. The composition of claim 2 wherein the metal M is nickel, copper, zinc, molybdenum, calcium or sodium.

4. The composition of claim 3 wherein up to about 3 moles of said heterocyclic nitrogen compound is used per mole of organometallic salt.

5. The composition of claim 4 where each x is N, Y is C and the alkyl groups in R'' and R''' contain 8 to 16 carbon atoms.

6. The composition of claim 5 wherein the metal in said organometallic salt is copper or zinc.

7. The composition of claim 6 wherein the R group in said organometallic salt is derived from $C_6$ to $C_{20}$ fatty acids.

8. The composition of claim 6 wherein the R group in said organometallic salt is derived from $C_{14}$ to $C_{20}$ fatty acids.

9. The composition of claim 8 wherein from about 0.1 to about 1% by weight of said complex, based on the total weight of the lubricating oil composition is used.

10. The composition of claim 9 wherein about 1 to about 2 moles of heterocyclic nitrogen compound is used per mole of organometallic salt.

11. The composition of claim 10 wherein said heterocyclic nitrogen compound is adenine and said organometallic salt is copper oleate.

* * * * *